United States Patent [19]

Berry, Jr.

[11] Patent Number: 4,588,533

[45] Date of Patent: May 13, 1986

[54] METHOD OF PREPARING ACYLOXYBENZENESULFONIC ACIDS AND SALTS THEREOF

[75] Inventor: C. Bernard Berry, Jr., Baton Rouge, La.

[73] Assignee: Ethyl Corporation, Richmond, Va.

[21] Appl. No.: 611,744

[22] Filed: May 18, 1984

[51] Int. Cl.$^4$ .......................................... C07C 143/525
[52] U.S. Cl. ...................... 260/402; 560/103; 560/109; 560/142; 260/505 E; 260/505 S; 260/505 N
[58] Field of Search ............... 260/402, 505 E, 505 S, 260/505 N; 560/142, 103, 109

[56] References Cited

U.S. PATENT DOCUMENTS

| 262,728 | 3/1939 | Guenther et al. | 260/402 |
| 1,823,815 | 9/1931 | Bertsch | 260/402 |
| 2,467,206 | 4/1949 | Gresham et al. | 560/130 |

FOREIGN PATENT DOCUMENTS 1563994  6/1976  United Kingdom ............... 260/402

OTHER PUBLICATIONS

Kirk–Othmer, *Encyclopedia of Chemical Technology*, vol. 19, (1969), pp. 280–281, John Wiley & Sons, Inc.

*Primary Examiner*—Charles F. Warren
*Assistant Examiner*—Elizabeth A. Flaherty
*Attorney, Agent, or Firm*—Donald L. Johnson; John F. Sieberth; Joseph D. Odenweller

[57] ABSTRACT

Alkali metal salts and alkaline earth metal salts of acyloxybenzenesulfonate are prepared by sulfonating an aryl ester of an organic acid with gaseous sulfur trioxide to produce a sulfonation reaction mixture containing acyloxybenzenesulfonic acid, neutralizing the sulfonation reaction mixture with alkali metal hydroxide or alkaline earth metal hydroxide to produce an alkali metal salt or alkaline earth metal salt of an acyloxybenzenesulfonic acid and thereafter recovering from the reaction mixture the acyloxybenzenesulfonic acid salt product thus formed.

20 Claims, No Drawings

METHOD OF PREPARING ACYLOXYBENZENESULFONIC ACIDS AND SALTS THEREOF

TECHNICAL FIELD

This invention relates to the production of alkali metal salts and alkaline earth metal salts of certain acyloxybenzenesulfonates. More particularly, this invention relates to the manufacture of alkali metal salts and alkaline earth metal salts of acyloxybenzenesulfonates by the steps of sulfonating an aryl ester with sulfur trioxide, neutralizing the resulting sulfonation product with an alkali metal hydroxide or an alkaline earth metal hydroxide and thereafter recovering from the reaction product the alkali metal salt or alkaline earth metal salt of acyloxybenzenesulfonate thus formed. The acyloxybenzenesulfonate salts of the present invention have many applications. For example, they are used in the textile industry as activators for the peroxide bleaching of fabrics and as dyeing assistants in the dyeing of acrylic fibers.

THE INVENTION

In a specific embodiment, and by way of illustration, the present invention contemplates the production of sodium 4-nonanoyloxybenzenesulfonate in accordance with the following equation:

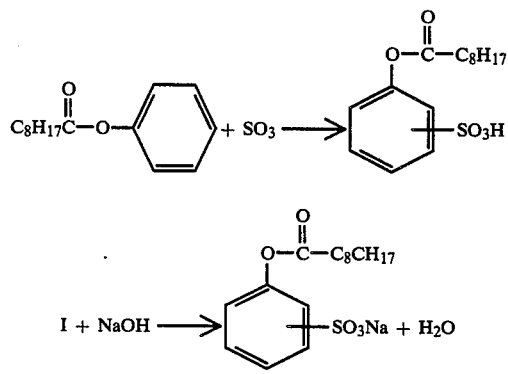

In other embodiments, the invention contemplates the production of alkali metal salts and alkaline earth metal salts of acyloxybenzenesulfonic acid of the formula:

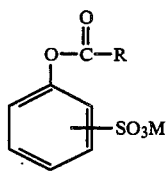

wherein R is a hydrocarbyl radical containing up to about 30 carbon atoms and is selected from alkyl, alkenyl, cycloalkyl, aryl, aralkyl, alkaryl and M is an alkali metal or an alkaline earth metal by reacting an aryl ester of the formula:

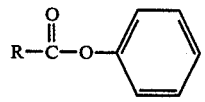

wherein R and M are as defined above with gaseous sulfur trioxide to form a sulfonation reaction mixture containing acyloxybenzenesulfonic acid of the formula:

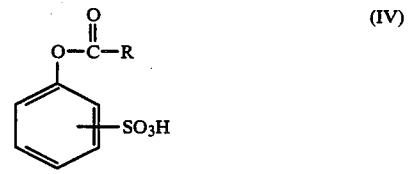

wherein R is as defined above, neutralizing the sulfonation reaction mixture containing the acyloxybenzenesulfonic acid produced thereby with alkali metal base or alkaline earth metal base to form the corresponding alkali metal salt or alkaline earth metal salt of acyloxybenzenesulfonate and thereafter recovering from the reaction mixture the acyloxybenzenesulfonate salt thus produced.

The aryl esters of the invention are known in the prior art as are methods for their preparation. For example, U.S. Pat. No. 2,467,206, incorporated herein by reference, discloses the synthesis of aryl esters of the formula acyl-OR', R' representing an aryl group, by heating an organic compound containing nonaromatic olefinic unsaturation with carbon monoxide and a phenol at elevated temperature and pressure in the presence of a catalyst containing, as an essential ingredient, cobalt or nickel.

Aelony, "Direct Esterification of Phenols with Higher Fatty Acids", *Journal of the American Oil Chemists' Society*, 32, 170–172 (1955), discloses a method of preparing fatty acid esters of many monohydric and dihydric phenols by direct esterification of the phenols with higher fatty acids at reaction temperatures between 115°–290° C., optionally in the presence of catalysts such as sulfuric acid, phosphoric acid, zinc stearate, lead stearate and triphenyl phosphite.

Representative examples of aryl esters which may be used in the present invention include:
phenyl formate;
phenyl acetate;
phenyl butyrate;
phenyl hexanoate;
phenyl heptanoate;
phenyl octanoate;
phenyl nonanoate;
phenyl decanoate;
phenyl undecanoate;
phenyl dodecanoate;
phenyl tridecanoate;
phenyl tetradecanoate;
phenyl pentadecanoate;
phenyl hexadecanoate;
phenyl octadecanoate;
phenyl eicosanoate;
phenyl docosanoate;
phenyl hexacosanoate;
phenyl triacontanoate;

phenyl acrylate;
phenyl 2-pentenoate;
phenyl 3-heptenoate;
phenyl 2-octenoate;
phenyl 3-octenoate;
phenyl 2-nonenoate;
phenyl 4-nonenoate;
phenyl 2-decenoate;
phenyl 4-decenoate;
phenyl 2-undecenoate;
phenyl 3-undecenoate;
phenyl 4-undecenoate;
phenyl 2-dodecenoate;
phenyl 3-dodecenoate;
phenyl 4-dodecenoate;
phenyl 2-eicosenoate;
phenyl 2-tricosenoate;
phenyl 2-triacontenoate;
phenyl benzoate;
phenyl phenylacetate;
phenyl phenylhexanoate;
phenyl phenylheptanoate;
phenyl phenyloctanoate;
phenyl phenylnonanoate;
phenyl phenyleicosanoate;
phenyl naphthoate;
phenyl cyclobutanecarboxylate;
phenyl cyclopentanecarboxylate;
phenyl cyclohexanecarboxylate;
phenyl cycloheptanecarboxylate;
phenyl cyclooctanecarboxylate;
phenyl cyclodecanecarboxylate;
phenyl cyclododecanecarboxylate;
phenyl 2-methylbenzoate;
phenyl 2-propylbenzoate;
phenyl 4-octylbenzoate;
phenyl 4-dodecylbenzoate;
phenyl 4-octadecylbenzoate;
mixtures thereof and the like.

Representative examples of the acyloxybenzenesulfonate salts products produced by the present process include:
benzenesulfonic acid, 2-hydroxy-,formate,sodium salt;
benzenesulfonic acid, 3-hydroxy-,formate,sodium salt;
benzenesulfonic acid, 3-hydroxy-,formate,calcium salt;
benzenesulfonic acid, 4-hydroxy-,formate,potassium salt;
benzenesulfonic acid, 4-hydroxy-,formate,calcium salt;
benzenesulfonic acid, 2-hydroxy-,acetate,potassium salt;
benzenesulfonic acid, 2-hydroxy-,acetate,calcium salt;
benzenesulfonic acid, 4-hydroxy-,acetate,calcium salt;
benzenesulfonic acid, 2-hydroxy-,propionate,potassium salt;
benzenesulfonic acid, 2-hydroxy-,propionate,calcium salt;
benzenesulfonic acid, 3-hydroxy-,propionate,potassium salt;
benzenesulfonic acid, 4-hydroxy-,propionate,sodium salt;
benzenesulfonic acid, 4-hydroxy-,propionate,potassium salt;
benzenesulfonic acid, 4-hydroxy-,hexanoate,sodium salt;
benzenesulfonic acid, 2-hydroxy-,heptanoate,sodium salt;
benzenesulfonic acid, 2-hydroxy-,heptanoate,potassium salt;
benzenesulfonic acid, 3-hydroxy-,heptanoate,sodium salt;
benzenesulfonic acid, 4-hydroxy-,heptanoate,sodium salt;
benzenesulfonic acid, 4-hydroxy-,heptanoate,potassium salt;
benzenesulfonic acid, 4-hydroxy-,heptanoate,calcium salt;
benzenesulfonic acid, 4-hydroxy-,octanoate,sodium salt;
benzenesulfonic acid, 2-hydroxy-,nonanoate,sodium salt;
benzenesulfonic acid, 2-hydroxy-,nonanoate,potassium salt;
benzenesulfonic acid, 2-hydroxy-,nonanoate,calcium salt;
benzenesulfonic acid, 3-hydroxy-,nonanoate,sodium salt;
benzenesulfonic acid, 4-hydroxy-,nonanoate,sodium salt;
benzenesulfonic acid, 4-hydroxy-,nonanoate,potassium salt;
benzenesulfonic acid, 4-hydroxy-,decanoate,sodium salt;
benzenesulfonic acid, 4-hydroxy-,dodecanoate,sodium salt;
benzenesulfonic acid, 4-hydroxy-,eicosanoate,sodium salt;
benzenesulfonic acid, 4-hydroxy-,triacontanoate,sodium salt;
benzenesulfonic acid, 4-hydroxy-,acrylate,sodium salt;
benzenesulfonic acid, 4-hydroxy-,but-2-enoate,sodium salt;
benzenesulfonic acid, 4-hydroxy-,hex-2-enoate,sodium salt;
benzenesulfonic acid, 4-hydroxy-,hex-3-enoate,sodium salt;
benzenesulfonic acid, 4-hydroxy-,hept-3-enoate,sodium salt;
benzenesulfonic acid, 4-hydroxy-,oct-2-enoate,sodium salt;
benzenesulfonic acid, 4-hydroxy-,oct-3-enoate,sodium salt;
benzenesulfonic acid, 4-hydroxy-,non-2-enoate,sodium salt;
benzenesulfonic acid, 4-hydroxy-,non-3-enoate,sodium salt;
benzenesulfonic acid, 4-hydroxy-,non-4-enoate,sodium salt;
benzenesulfonic acid, 4-hydroxy-,dodec-2-enoate,sodium salt;
benzenesulfonic acid, 4-hydroxy-,eicos-2-enoate,sodium salt;
benzenesulfonic acid, 4-hydroxy-,triacont-2-enoate,sodium salt;
benzenesulfonic acid, 4-hydroxy-,benzoate,sodium salt;
benzenesulfonic acid, 4-hydroxy-,benzoate,calcium salt;
benzenesulfonic acid, 4-hydroxy-,phenylacetate,potassium salt;
benzenesulfonic acid, 4-hydroxy-,phenylhexanoate,sodium salt;
benzenesulfonic acid, 4-hydroxy-,phenyleicosanoate,sodium salt;
benzenesulfonic acid, 4-hydroxy-,naphthoate,potassium salt;
benzenesulfonic acid, 4-hydroxy-,naphthoate,calcium salt;

benzenesulfonic acid, 4-hydroxy-,cyclobutanecarboxylate,sodium salt;
benzenesulfonic acid, 4-hydroxy-,cyclohexanecarboxylate,sodium salt;
benzenesulfonic acid, 4-hydroxy-,cyclooctanecarboxylate,sodium salt;
benzenesulfonic acid, 4-hydroxy-,cyclododecanecarboxylate,sodium salt;
benzenesulfonic acid, 4-hydroxy-,2-methylbenzoate,-sodium salt;
benzenesulfonic acid, 4-hydroxy-,3-ethylbenzoate,-sodium salt;
benzenesulfonic acid, 4-hydroxy-,4-octylbenzoate,-sodium salt;
and mixtures thereof.

The sulfonation process according to the present invention may be carried out by employing either the continuous thin falling film sulfonation system or the stirred batch sulfonation system. In the continuous falling film process the sulfur trioxide is used as a gas reactant. It can be used alone in undiluted form or along with a diluent such as any of the commonly used inert gases, e.g., nitrogen, air, helium, argon, etc. Normally, the sulfonating agent enters the system in such a state that sulfur trioxide is diluted with inert gases to a concentration of 1 to 20% by volume sulfur trioxide.

The sulfur trioxide can be derived from any convenient source; for example, from the burning of sulfur, or from conventional oleum stripping. Stabilized sulfur trioxide also can be used, but the particular stabilizing agents such as tertiary butyl phosphate, boron and phosphorus compounds represent a non-essential compound to the reaction system. If stabilized sulfur trioxide is used in the process, the stabilizing agent should be removed from the sulfur trioxide before it is added to the reaction system.

The mole ratio of sulfur trioxide to aryl ester reactant used in the process ordinarily ranges from about 1:1 to about 3:1.

The introduction temperature of the gaseous sulfur trioxide should be at least 50° F. since below this temperature the sulfur trioxide may condense to liquid form thereby possibly clogging the reactor. In most cases, the sulfur trioxide is introduced at a temperature within 20° F. either above or below the aryl ester introduction temperature, provided such sulfur trixoide introduction temperature exceeds the above-specified minimum of at least 50° F. Preferably, the gaseous sulfuric trioxide is introduced into the reaction zone at room temperature, e.g., about 80° F.

Typically, the reaction is carried out at atmospheric pressure; however, higher pressurers up to about 100 psig or higher, can be used if desired. There is no real advantage, however, in carrying out the reaction at pressures exceeding atmospheric.

In one form of the falling film process, the aryl ester is fed at a metered rate to the top of a vertical tubular reactor in a manner such that the aryl ester flows down the inner walls of the tubular reactor as a thin film. Gaseous sulfur trioxide in an inert diluent such as nitrogen is fed at the top of the reactor such that it also passes down through the tubular reactor and contacts the thin film of aryl ester. Temperature can be controlled by applying heat or coolant to the outside of the tubular reactor. The effluent at the bottom of the reactor is separated to remove gas from liquid and the gas phase is passed to an alkaline scrubber to remove unreacted sulfur trioxide. The liquid phase contains the sulfonated aryl ester which is recovered by neutralization of the sulfonic acid groups with alkali or alkaline earth metal based and extraction of unreacted aryl ester and other impurities with an inert organic solvent such as hexane or petroleum ether.

Although not required, it is preferred that the process be carried out under substantially anhydrous conditions, and accordingly, the components of the reaction system are brought together and maintained under a substantially dry, inert atmosphere. It is not necessary, however, that the reagents used in the process be anhydrous before they are combined as any water present in the reagents can be removed by conventional techniques, such as, for example, by azeotropic distillation of the combined reagents using an organic solvent such as hexane, octane, toluene, xylenes and the like.

Typically, compounds other than the desired acyloxybenzenesulfonate salts are co-produced by the process of the invention. The reaction mixture can contain unreacted starting material, disulfonated products, alkali metal-p-hydroxybenzenesulfonates and alkaline earth metal p-hydroxybenzenesulfonates. However, as set forth in the examples, the yield of acyloxybenzenesulfonate salt may be as high as 70 weight percent and above. Removal of unreacted starting material from the reaction mixture may be readily effected by solvent extraction. An inert liquid is employed as a reaction medium in the batch reaction. It is advantageous but not necessary, that the particular solvent used have a boiling point higher than the desired reaction temperature. Examples of solvents which may be used in the process include chlorinated hydrocarbons, especially chlorinated aliphatic hydrocarbons such as methylene chloride, carbon tetrachloride, etc. Additionally, aprotic solvents such as triglyme, tetraglyme, 1,2-diethoxyethane and dipolar aprotic solvents such as N,N-dimethylacetamide, tetramethylene sulfone, N-methylpyrrolidinone and like materials may also be used.

The batch process can be carried out by charging a solution of aryl ester to a reactor and feeding sulfur trioxide to the aryl ester solution. The sulfur trioxide may be gaseous or dissolved in a liquid. This liquid can be the same solvent as used to dissolve the aryl ester. The sulfur trioxide reaction can be conducted over a wide temperature range. The temperature should be high enough to cause the sulfonation reaction to proceed at a reasonable rate but not so high as to cause excessive degradation of the reactants or products. A useful sulfonation temperature range is about 10°–150° C. A preferred range is about 20°–75° C.

The sulfonation reaction mixture resulting from the sulfonation steps of the invention is subjected to neutralization with an alkali or alkaline earth metal inorganic base. As mentioned previously, the mixture contains acyloxybenzenesulfonic acids as well as disulfonated product, unreacted aryl ester and other impurities. The neutralization step is directed toward the neutralization of the acyloxybenzenesulfonic acid contained in the reaction mixture and therefore it is preferred to avoid hydrolysis of ester groups in this step. This is because when the hydrolysis of ester groups takes place in the neutralizing step, solvent extraction of the unreacted phenol ester is very difficult.

Useful neutralizing agents are alkali metal or alkaline earth metal hydroxides, oxides, carbonates, acid carbonate and the like. Alkali and alkaline earth metal hydroxides are preferred, specifically, LiOH, NaOH, KOH, RbOH, $Ca(OH)_2$, and $Mg(OH)_2$. Sodium hydroxide is particularly preferred. The quantity of basic reagents employed in the neutralizing step is that amount sufficient to be capable of neutralizing the acyloxybenzenesulfonic acid contained in the sulfonation reaction mixture to a pH of about 4–6. The neutralization reaction can be carried out at a temperature of from about 10° C. to about 80° C.

The neutralization can be conducted using an aqueous solution of slurry of the inorganic base. For example, an aqueous solution of NaOH can be added to the sulfonated aryl ester until the pH is in the 4–6 range. Excess caustic should be avoided because it can saponify the ester group to the original fatty acid and phenol. Likewise, the temperature should be kept low to minimize saponification, e.g., 10°–30° C.

In another neutralization procedure the sulfonated aryl ester is mixed with a solution or slurry of the inorganic base in a polar organic solvent such as lower alcohols, dimethylformamide, dimethylsulfoxide, and the like. Examples of the preferred polar solvents are alcohols such as methanol, ethanol, isopropanol and the like. Of these, isopropanol is preferred.

The neutralized mixture resulting from the neutralizing step is subjected to solvent extraction.

The following examples illustrate how the process can be carried out.

EXAMPLE 1

In a stirred reaction vessel was placed 82.5 g (0.375 moles) of phenyl octanoate. A nitrogen stream containing 3.2 volume percent sulfur trioxide was injected into the stirred aryl ester at 20° C. Total sulfur trioxide uptake was 0.352 moles. The sulfonated mixture had an acid number of 196.4. The product was neutralized with aqueous sodium hydroxide to a pH of 5 and then extracted with petroleum ether to remove nonsulfonated materials. The resultant product assayed 70.1 wt% octanoylbenzene sulfonate, mostly para isomer.

EXAMPLE 2

In a stirred reactor was placed 10.3 g of phenol heptanote (30% branched chain acid) and 30 ml of 1,2-dichloroethane. To this was added slowly at −10° C. a solution of 4.4 g sulfur trioxide in 20 ml 1,2-dichloroethane over about an hour period. The reaction mixture was allowed to warm to room temperature. A small sample was taken. The mixture was then refluxed one hour at 81°–85° C. The sample was analyzed by NMR as follows:
Heptanoyloxybenzene sulfonic acid: 75%
α-methyl branched product: 12%
Phenyl heptanoate: 10%

EXAMPLE 3

This example was run in the same manner as Example 2 through the addition of sulfur trioxide solution at about −10° C. over a 71 minute period. Following this, the unreacted sulfur trioxide was removed by bubbling nitrogen through the solution at room temperature. Solvent was removed by vacuum strip at room temperature leaving 14.91 g of residue. The residue was dissolved in methyl ethyl ketone. Then 25 ml of water and three drops of phenolphthalein was added. The solution was cooled in an ice bath and a solution of 2 g sodium hydroxide in 25 ml water was added. The neutral mixture was then extracted four times with 50 ml portions of petroleum ether. The solution was then evaporated to dryness under vacuum leaving a 16.39 g residue which was analyzed by NMR and found to contain 46.6 wt% sodium heptanoyloxybenzenesulfonate. A portion of the product was apparently lost by hydrolysis of the acyloxy ester group during work-up forming sodium phenylsulfonate and fatty acid.

EXAMPLES 4–8

A series of falling-film sulfonations were carried out in a 55 cm long vertical straight glass tubular reactor. Phenyl nonanoate was flowed down the inside surface of the glass tube at a rate of 10 ml each three minutes. A nitrogen stream containing three volume percent sulfur trioxide was passed down through the glass tube at a rate of 12 liters per minute giving a 30% molar excess of sulfur trioxide. The phenyl ester was preheated to reduce viscosity. Temperatures in the glass tube were controlled by a water jacket. The effluent at the bottom of the column was separated into a gas and liquid phase and the liquid phase was continuously neutralized to a pH of 4–6 using 30% aqueous sodium hydroxide. In Examples 6–8, a post-reactor was placed between the tubular reactor and the gas-liquid separator to increase contact time between the sulfur trioxide and aryl ester. The post-reactor consisted of a glass vessel fitted with one or more fritted glass plates. The sulfur trioxide-organic mixture was forced up through the fritted glass plates by gas pressure and then flowed into the gas-liquid separator.

Reaction conditions and results are given in the following table:

|  | Example | | | | |
| --- | --- | --- | --- | --- | --- |
|  | 4 | 5 | 6 | 7 | 8 |
| Reactor temp ° C. | 70 | 70 | 50 | 70 | 70 |
| Pre-heat temp ° C. | 40 | 70 | 70 | 70 | 70 |
| Post reactor temp ° C. | — | — | $A^1$ | $A^1$ | 70 |
| Unreacted ester % | 22 | 20 | 30 | 20 | 8 |
| Product assay$^2$ % | 90 | 90 | 90 | 90 | 80 |

[1]ambient temperature
[2]by HPLC

EXAMPLE 9

Another falling-film sulfonation was conducted at 70° C. feeding phenyloctanoate. The liquid effluent from the reactor was de-gassed by nitrogen injection and the organic phase was passed directly into an organic solvent containing a slurry of sodium carbonate. The solvents tried were hexane and ethanol. The neutralized octanoylbenzenesulfonic acid precipitated and non-sulfonated products stayed in solution. The neutralization in hexane was incomplete. In the polar alcohol solvent neutralization was much better and the precipitate assayed about 50% sodium salt of octanoylbenzenesulfonic acid, para isomer.

I claim:

1. A process for making an acyloxybenzene sulfonic acid, said process comprising reacting an aryl ester of an organic acid said ester having the formula:

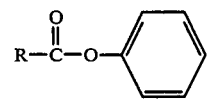

wherein R is a hydrocarbon radical containing up to 30 carbon atoms and is selected from the group consisting of alkyl, alkenyl, cycloalkyl, aryl, arylalkyl and alkaryl with sulfur trioxide to form said acyloxybenzene sulfonic acid.

2. A process of claim 1 wherein R is an alkyl group.

3. A process of claim 2 wherein said alkyl group contains about 5–11 carbon atoms.

4. A process of claim 3 wherein said alkyl group is a substantially linear alkyl group.

5. A process for making an alkali metal or alkaline earth metal salt of an acyloxybenzene sulfonic acid, said process comprising (A) reacting an aryl ester of an organic acid having the formula

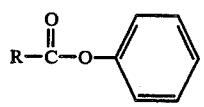

wherein R is a hydrocarbon radical containing up to 30 carbon atoms and is selected from the group consisting of alkyl, alkenyl, cycloalkyl, aryl, aryalkyl and alkaryl with sulfur trioxide to form an acyloxybenzene sulfonic acid;

(B) neutralizing the sulfonic acid groups on said acyloxybenzene sulfonic acid with an alkali metal or alkaline earth metal base selected from oxides, hydroxides, carbonates and acid carbonates to form said alkali metal or alkaline earth metal salt of an acyloxybenzene sulfonic acid; and (C) recovering said acyloxybenzene sulfonic acid salt.

6. A process of claim 5 wherein R is an alkyl group.

7. A process of claim 6 wherein said alkyl group contains about 5–11 carbon atoms.

8. A process of claim 7 wherein said alkyl group are substantially linear alkyl groups.

9. A process of claim 5 wherein the neutralizing of said sulfonic acid group is done using an alkali metal hydroxide, carbonate or acid carbonate.

10. A process of claim 9 wherein said neutralizing of said sulfonic acid groups is done with an alkali metal hydroxide.

11. A process of claim 10 wherein said neutralizing of said sulfonic acid groups is done with an aqueous solution of an alkali metal hydroxide.

12. A process of claim 11 wherein said alkali metal hydroxide is sodium hydroxide.

13. A process of claim 9 wherein the neutralization of said sulfonic acid groups is done using a solution or slurry of an alkali metal hydroxide or carbonate in a polar solvent.

14. A process of claim 13 wherein said polar solvent is a lower alcohol.

15. A process of claim 14 wherein said alcohol is selected from methanol, ethanol and isopropanol.

16. A process of claim 11 wherein R is an alkyl containing 5–11 carbon atoms.

17. A process of claim 12 wherein R is an alkyl containing about 5–11 carbon atoms.

18. A process of claim 9 wherein said neutralizing of said sulfonic acid groups is done using a solution or slurry of an alkali metal hydroxide or carbonate in a polar solvent.

19. A process of claim 18 wherein said polar solvent is a lower alcohol.

20. A process of claim 19 wherein said lower alcohol is methanol, ethanol or isopropanol.

* * * * *